United States Patent [19]

Goddard et al.

[11] Patent Number: 5,718,716

[45] Date of Patent: Feb. 17, 1998

[54] PROCESS FOR MANUFACTURING SUTURES FROM COPOLYMERS OF GLYCOLIDE AND ε-CAPROLACTONE

[75] Inventors: Hwason Goddard, Somerville; Kenneth M. Keilman, Raritan; Oliver S. Sosely, Middlesex, all of N.J.

[73] Assignee: Ethicon, Inc., Somerville, N.J.

[21] Appl. No.: 710,613

[22] Filed: Sep. 20, 1996

[51] Int. Cl.$^6$ .................................................. A61B 17/04
[52] U.S. Cl. .................. 606/230; 264/210.7; 264/210.8; 264/235.6; 264/342 RE
[58] Field of Search ........................ 264/555–557, 264/210.7, 210.8, 235.6, 342 RE; 606/230, 231

[56] References Cited

U.S. PATENT DOCUMENTS

| | | | |
|---|---|---|---|
| 4,605,730 | 8/1986 | Shalaby et al. | 528/357 |
| 4,700,704 | 10/1987 | Jamiolkowshi et al. | 606/230 |
| 4,911,165 | 3/1990 | Lennard et al. | 606/231 |
| 5,133,739 | 7/1992 | Bezwada et al. | 606/230 |
| 5,217,485 | 6/1993 | Liu et al. | 606/231 |
| 5,322,925 | 6/1994 | Muth et al. | 606/231 |
| 5,540,717 | 7/1996 | Lui et al. | 606/231 |
| 5,554,170 | 9/1996 | Roby et al. | 606/231 |
| 5,587,122 | 12/1996 | Lennard | 264/178 |

*Primary Examiner*—Gary Jackson
*Attorney, Agent, or Firm*—Hal Brent Woodrow

[57] ABSTRACT

We have discovered a process for producing a suture from copolymers of glycolide and ε-caprolactone comprising the steps of (a) extruding a melted copolymer of a glycolide and ε-caprolactone resin through an orifice and rapidly quenching the melted copolymer resin to produce a filament; (b) drawing the filament in the range of from about 4× to about 7.5× to produce a singly drawn filament; (c) drawing the singly drawn filament in the range of form about 1× to about 3× in a first heated zone being maintained at a temperature in the range of from about 150° F. to about 450° F., to form a doubly drawn filament; (d) shrinking the doubly drawn filament in the range of from about 0.75 percent to about 0.98 percent, in a second heated zone being maintained at a temperature in the range of from about 100° F. to about 400° F., to form a relaxed filament then rack annealing the relaxed filament to form a glycolide/ε-caprolactone suture.

10 Claims, 1 Drawing Sheet

PROCESS FOR MANUFACTURING SUTURES FROM COPOLYMERS OF GLYCOLIDE AND E-CAPROLACTONE

FIELD OF THE INVENTION

This invention relates to the field of suture manufacture and more specifically it relates to a process for making sutures from copolymers of glycolide and ε-caprolactone.

BACKGROUND OF THE INVENTION

Copolymers of glycolide and caprolactone have been described by Jamiolkowski et al. in U.S. Pat. Nos. 4,605,730 and 4,700,704 and by Bezwada et al. in U.S. Pat. No. 5,133,739 (all hereby incorporated by reference). As disclosed by Jamiolkowski and Bezwada, these copolymers may be processed into monofilament sutures which are exceptionally compliant while retaining significant straight tensile strength and knot strength. Jamiolkowski discloses that these glycolide/ε-caprolactone copolymers may be made into sutures by extruding the copolymer into a filament then orienting (stretching or drawing) the filament in a two-step process and annealing the filament for 5 to 16 hours. The fibers disclosed by Jamiolkowski with the lowest Young's Modulus values (under 200 Kpsi) would be expected to be the most compliant fibers.

Bezwada et al. also discloses glycolide/ε-caprolactone copolymers which are produced by reacting a prepolymer of ε-caprolactone and glycolide with additional glycolide.

Bezwada describes these copolymer as having very low Young's Modulus values and desirable strength and knot tensile strengths.

However, it would be desirable to optimize the process used for manufacturing sutures from these copolymers with high straight and knot tensile strengths and low Young's Modulus values.

SUMMARY OF THE INVENTION

We have discovered a process for producing a suture comprising the steps of (a) extruding melted copolymer composed substantially of glycolide and ε-caprolactone resin through an orifice and rapidly quenching the melted copolymer resin to produce a filament; (b) drawing the filament in the range of from about 4× to about 7.5× in a first drawing zone to produce a drawn filament; (c) drawing the singly drawn filament in a second drawing zone in the range of from about 1× to about 2.5× while in a first heated zone being maintained at a temperature in the range of from about 150° F. to about 450° F., to form a doubly drawn filament; (d) relaxing the doubly drawn filament in the range of from about 0.75× to about 0.98×, in a second heated zone being maintained at a temperature in the range of from about 122° F. to about 300° F., to form a relaxed filament; then rack annealing the relaxed filament.

BRIEF DESCRIPTION OF THE FIGURES

The FIGURE is a side elevation, partially schematic of an apparatus suitable for carrying out the process of the present invention.

DETAILED DESCRIPTION OF THE INVENTION

Figure 1:
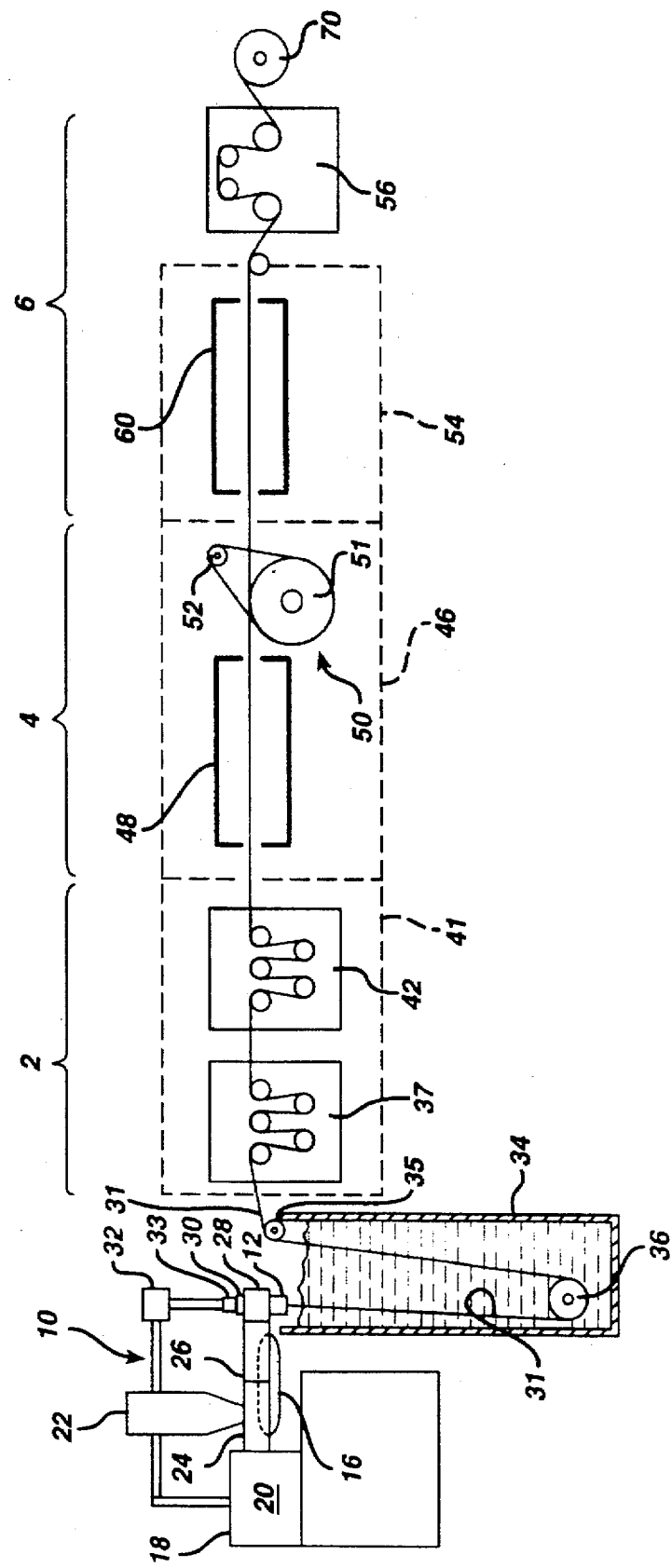

As used herein the term glycolide/ε-caprolactone copolymers shall include copolymers composed primarily of repeating units having the chemical formula I and II:

$$[-O-(CH_2)_5-C(O)-]_A \qquad I$$

$$[-O-(CH_2)-C(O)-]_B \qquad II$$

Preferred are the glycolide/ε-caprolactone copolymers described in U.S. Pat. Nos. 4,605,730; 4,700,704 and 5,133,739 assigned to Ethicon, hereby incorporated by reference). However, minor amounts (i.e. less than 10% by weight and preferably less than 5% by weight) of other aliphatic ester monomers may also be present in these copolymers. Suitable additional repeating units include $[-O-R_5-C(O)-]$ where $R_5$ is selected from the group consisting of $-C(R_6)(R_7)-$, $-(CH_2)_3-O-$, $-CH_2-CH_2-O-CH_2-$, $-CR_8H-CH_2-$, $-(CH_2)_F-O-C(O)-$ and $-(CH_2)_F-C(O)-CH_2-$; $R_6$ and $R_7$ are independently hydrogen or an alkyl containing from 1 to 8 carbon atoms, provided that $R_6$ and $R_7$ are not both hydrogen; $R_8$ is hydrogen or methyl and F is an integer in the range of from 2 to 6. Suitable aliphatic esters repeating units include but are not limited to repeating units selected from the group consisting of p-dioxanone, trimethylene carbonate, lactide, 1,5-dioxepan-2-one, 1,4-dioxepan-2-one and 6,6-dimethyl-1,4-dioxepan-2-one.

The preferred method for preparing the flexible glycolide/ε-caprolactone sutures of the present invention utilizes as the raw material pellets of glycolide/ε-caprolactone copolymer (prepared as described by Bezwada) having a weight average molecular weight of from about 59,000 MW to about 100,000 MW and has a crystallinity of greater than 10 percent and preferably greater than 15 percent as measured by x-ray diffraction.

Referring to the FIGURE, there is shown an apparatus that is suitable for carrying out the present invention. An extruder 10 is terminated at one end with an extrusion die 12. A longitudinal extruder screw is mounted for rotation within the barrel 16 and is driven by a variable speed motor 18 through a gear 20. Polymer pellets are introduced into the extruder through hopper 22 which communicates with the barrel 16. In normal operation of the extruder 10, the feeding zone 24 of the extruder is maintained at a temperature in the range of from about 350° F. to about 450°0 F., the transition zone 26 is maintained at a temperature in the range of from about 350° F. to about 450° F., and the pump block 30, block 28 and die 12 are maintained at a temperature in the range of from about 340° F. to about 500° F. A pump 33 driven by a motor 32, pumps the molten copolymer through spinneret orifices in the die 12 to form a plurality of filaments 31 (for simplicity only one filament is shown in the FIGURE). The filament 31 is extruded into quench bath 34. The quench bath 34 is filled with a liquid heat exchange medium. The surface of the liquid in the quench bath 34 is preferably not more than a few centimeter below the die 12 in order to achieve rapid cooling of the extruded filament 31. Preferably, the gap will be in the range of from about ¼" to about 7". The quench bath 34 is maintained at a temperature below 120° F. and preferably the quench bath 34 is maintained at about room temperature. The filament 31 enters the quench bath 34 and travels around idler roll 36 in the quench bath 34 and then up out of the quench bath 34 to another idle roller 35 then to the first godet 37 in the first drawing zone 2. In the first drawing zone 2 the filament 31 is drawn in the range of from about 1× to 8× its original length. The filament 31 may be drawn incrementally or in several discrete steps in the first drawing zone 2. The drawing may preferably be performed in a heated cabinet, or by using heated godets).

In the preferred embodiment of the invention shown in the attached FIGURE, the filament 31 is drawn by a first godet 37 and a second godet 42. The first godet 37 includes several roll 38. The first godet 37 is rotated at a peripheral speed that is equal to or slightly higher than the speed at which the filament 31 is extruded from the die orifice 12. The first godet 37 may be combined with a nip roller (not shown) to assure the filament 31 does not slip in the subsequent drawing to the extruded filament 31. The first draw of the extruded filament 31 will be performed by feeding the extruded filament 31 from the first godet 37 to second godet 42 which includes several rolls 43. The second godet 42 is rotated at a peripheral speed that is in the range of from about 1× to about 8× of the speed of the first godet 37.

The filament 31 then passes into a second drawing zone 4, where the filament 31 is drawn again in the range of from about 1× to about 4× while in a first heated zone 46. The filament 31 may be drawn incrementally or in one or more discrete steps in the second drawing zone 4. The drawing will be performed in a first heated zone 46. The temperature of the first heated zone 46 will be in the range of from about 150° F. to about 450° F., preferably in the range of from about 175° F. to about 400° F. The filament 31 will remain in the second heated zone 46 generally only a short time preferably in the range of from about 1.0 seconds to about 30 seconds.

In the preferred embodiment of the invention shown in the attached FIGURE, the filament 31 passes through a second heated zone 46 to a third godet 50. The first heated zone 46 is preferably an orienting oven 48. The filament 31 is drawn in the range of from about 1× to about 3×, while traveling from the second godet 42 to the third godet 50 in the second heated zone 46. The third godet 50 includes a main roll 51 and an air bearing 52, that are rotating at a peripheral speed of about 1× to about 3× of the peripheral speed of the second godet 42. Preferably the draw ratio will be in the range of from about 1× to about 3×.

The filament 31 then passes from the second drawing zone 4 into an annealing zone 6, where the filament 31 is annealed and allowed to shrink. In the annealing zone 6 the filament 31 is placed in a second heated zone 54 that is maintained at a temperature in the range of from about 100° F. to about 400° F. wherein the filament is allowed to shrink to the range of from about 98 percent to about 65 percent and preferably from about 95 to about 75 percent of the filament original length. The filament 31 may be allowed to shrink incrementally or in one or more discrete steps in the second heated zone 54. The filament 31 will remain in the third heated zone 54 for a short time generally in the range of from about 1.0 to about 30 seconds and preferably in the range of from about 3.0 seconds to 20 seconds.

In the preferred embodiment of the present invention shown in the attached FIGURE, the filament 31 passes through a second heated zone 54 to a fourth godet 56. The heated zone 54 is preferably an annealing oven 60. The fourth godet 56 includes several rolls 57 that are rotating at a peripheral speed of about 8× to about 0.98× of the peripheral speed of the third godet 50. Preferably the relaxation ratio will be in the range of from about 0.75 to about 0.9×. After passing around the fourth godet 56, the filament 31 is then wound on a spool 70 and transferred to a creel or rack for additional annealing.

The overall draw ratio, that is, the difference between the peripheral speed of the fourth godet 56 and the first godet 37, will ordinarily be from about 6× to about 8× and preferably the total draw ratio will be in the range of from about 6.9× to about 7.2×.

The residence time of filament 31 within any of the heated zones can be optimized to improve fiber properties. The overall residence time that filament 31 is present in the first and second heated zones will preferably be in the range of from about 2 seconds to about 50 seconds and most preferably in the range of from about 4 seconds to about 30 seconds. The residence time can be increased with longer ovens or by having multiple wraps of the fiber in the oven.

Suitable creels or racks for annealing filament 31 have been described in the art such as the creels disclosed by Listner et al. in U.S. Pat. No. 3,630,205 (which is hereby incorporated by reference herein). However, unlike the creels disclosed by Listner which permit the filaments to contract as they are annealed in the present invention, it is preferred to fix both ends of the creel and anneal the filaments with no relaxation. Once wrapped on the creel the filament should be annealed in an oven at a temperature of in the range of from about 85° C. to from about 125° C. The filaments should be annealed for in range of from and preferably about 4 hours to about 8 hours. The filaments may be removed from the creel by cutting the filaments at opposite ends of the creel. The filaments may be attached to needles, packaged and sterilized (by ethylene oxide or other appropriate techniques).

The following non-limiting examples are further provided to illustrate the practice of the present invention.

EXAMPLE

A dyed 75/25 weight percent glycolide/caprolactone segmented block copolymer made as described in U.S. Pat. No. 5,133,739 was used to produce surgical sutures under the conditions set forth in Table 1 below.

The polymer was generally made by adding into a dry 15 gallon reactor provided with agitator and oil circulating jacket 7406 grams (64.9 moles) of ε-caprolactone, 9205 grams (79.3 moles of glycolide), 19.71 ml. (0.207 moles) of diethylene glycol (DEG) and 13.68 ml. (0.0045 moles) of stannous octoate (0.33 molar solution in toluene). The reactor contents are evacuated and the vacuum is released with nitrogen. The evacuation and vacuum release cycle is repeated once more, each cycle lasting approximately 25 minutes. The circulating heating oil temperature is set at 195° C. and the batch temperature is monitored. This first stage polymerization reaction is allowed to proceed for 6 hours measured from the time that the batch temperature reaches 190° C. The oil temperature is increased to 216° C. and 13389 grams (115.4 moles) of molten glycolide is added from a melt tank with agitation. After 10 minutes the oil temperature is reset to 204° C. Approximately 60 minutes after the addition of the molten glycolide, the batch temperature begins to be greater than the oil temperature. This point is referred to as the crossover point (XO) and is selected as the "zero time" for the second stage exothermic reaction. At 70 minutes from zero time, the bottom gate of the reactor is opened, the oil is set at 212° C. and the polymer is forced into the pelletizer system. The reactor contents are discharged in 25 minutes.

The polymer is then pelletized using a cutter speed maintained in the range of 3000 to 3100 RPM. A four blade cutter is used. The die holes are 0.11" in diameter and 12 open holes are used. The tempering water recirculation rate is 60 gallons/minute and the water is maintained at 13° C. The copolymer pellets are separated from the water by means of a centrifugal dryer. The pellets are dried in a vacuum tumble dryer provided with a heating jacket. The drying cycle is 18 hours at room temperature followed by 24 hours at 110° C. The copolymer had an inherent viscosity of 1.66 dl/g measured in hexafluoroisopropanol. The molecular weight by Gel Permeation Chromatography was MW=82, 000 daltons. The melting point was 214° C. The composition determined by NMR was 24.5 mole % polycaprolactone, PCL, and 74.7 mole % polyglycolic acid, PGA. The polymers made in this manner were then extruded into filaments under the following conditions:

TABLE 1

| Sample No. | 1 | 2 | 3 | 4 | 5 | 6 |
|---|---|---|---|---|---|---|
| Polymer IV | 1.85 | 1.85 | 1.85 | 1.85 | 1.85 | 1.85 |
| Filament Size | 1 | 1 | 1 | 1 | 1 | 1 |
| Feed Zone °F. | 400 | 400 | 400 | 400 | 400 | 400 |
| Transition Zone °F. | 400 | 400 | 400 | 400 | 400 | 400 |
| Pump °F. | 470 | 470 | 470 | 470 | 470 | 470 |
| Block °F. | 470 | 470 | 470 | 470 | 470 | 470 |
| Die °F. | 480 | 470 | 480 | 470 | 470 | 470 |
| Barrel PSI | 1503 | 1505 | 1503 | 1502 | 1502 | 1502 |
| Pump PSI | 2391 | 2042 | 2532 | 2853 | 2853 | 2853 |
| Die PSI | 375 | 400 | 418 | 463 | 463 | 463 |
| Pump RPM | 6.6 | 6.8 | 7.0 | 6.9 | 6.9 | 6.9 |
| Air Gap inches | 2 | 2 | 2 | 2 | 2 | 2 |
| Quench Bath °F. | 68 | 68 | 68 | 68 | 68 | 68 |
| Screw RPM | 6.5 | 6.6 | 6.7 | 6.6 | 6.6 | 6.6 |
| Godet 1 FPM/°F. | 16 | 16 | 16 | 16 | 16 | 1.6 |
| Godet 2 FPM/°F. | 85 | 85 | 85 | 85 | 85 | 85 |
| Orienting Oven °F. | 350 | 350 | 350 | 400 | 400 | 400 |
| Godet 3 FPM/°F. | 110 | 110 | 115 | 115 | 115 | 115 |
| Annealing Oven °F. | — | 250 | 250 | 175 | 175 | 175 |
| Godet 4 FPM/°F. | — | 98 | 104 | 104 | 104 | 104 |
| Total Draw Ratio | 6.88 | 6.88 | 7.19 | 7.19 | 7.19 | 7.19 |
| % of In-Line Relaxation | N/A | 10% | 10% | 10% | 10% | 10% |

RPM is revolutions per minute.
FPM is feet per minute.
[1]The original data page appears to have reversed these numbers.

TABLE 2

|  | GAUGE LENGTH (cm) | CHART SPEED(cm) | CROSSHEAD SPEED (cm/min.) |
|---|---|---|---|
| STRAIGHT TENSILE | 12.7 | 30.5 | 30.5 |
| KNOT TENSILE | 12.7 | 30.5 | 30.5 |
| BREAK ELONGATION | 12.7 | 30.5 | 30.5 |

The straight tensile strength was calculated by dividing the force to break by the initial cross-sectional area of the suture. The elongation at break was read directly from the stress-strain curve of the sample.

The knot tensile strength of a suture was determined in separate tests. The surgeon's knot was a square knot in which the free end was first passed twice, instead of once, through the loop, and the ends drawn taut so that a single knot was superimposed upon a compound knot. The first knot was started with the left end over the right end and sufficient tension was exerted to tie the knot securely.

The specimen was placed in the INSTRON Tensile Tester with the knot approximately midway between the clamps. The knot tensile strength was calculated by dividing the force required to break by the initial cross-sectional area of the fiber. The tensile strength values are reported in KPSI ($PSI \times 10^3$).

TABLE 3

Comparison of In-line and Rack Annealed Properties

| Sample No. | Size | Diameter (mils) | Tensile lbs. | Strength Kpsi | Knot lbs. | Strength Kpsi | Elonga-tion % | Modulus Kpsi |
|---|---|---|---|---|---|---|---|---|
| 1 | 1 | 20.95 | 34.63 | 100.5 | 17.91 | 52.0 | 46.47 | 107.7 |
| 2 | 1 | 20.91 | 36.39 | 105.9 | 17.43 | 50.8 | 40.85 | 117.7 |
| 3 | 1 | 21.06 | 39.27 | 112.8 | 19.12 | 54.9 | 40.78 | 111.2 |
| 4 | 1 | 20.91 | 39.82 | 116.0 | 17.97 | 52.3 | 38.73 | 122.3 |
| 5 | 1 | 20.86 | 37.72 | 110.4 | 18.33 | 53.6 | 37.28 | 95.9 |
| 6 | 1 | 20.85 | 37.74 | 110.5 | 19.18 | 56.2 | 38.01 | 103.5 |

Extruded filaments 1–6 were wound on racks and annealed. Sample I was wound on a rack which allowed the filaments to shrink 10% during the annealing process. Samples 2–5 were wound on racks which did not allow the filaments to shrink during the annealing process. Samples 1–4 were annealed at 105° C. for six (6) hours. Samples 5 and 6 were annealed at 120° C. and 125° C. respectively for six (6) hours. All the samples were tested using the following test procedures. The data from these test are presented in Table 2.

The characteristic properties of samples 1–6 were determined by conventional test procedures. The tensile properties (i.e., straight and knot tensile strengths and elongation) displayed herein were determined with an INSTRON Tensile Tester. The settings used to determine the straight tensile, knot tensile and break elongation were the following, unless indicated:

Sample Numbers 2–6 were produced by the inventive in-line annealing process described above. Sample 1 was produced by rack annealing the sutures following conventional manufacturing procedures. The data above demonstrates that the inventive process produces sutures that have approximately a 10% increase in the tensile strengths without significantly increasing the Young's modulus of the sutures.

As shown in Table 4 below the BSR profile of the inventive process also improved as compared to the current process used to manufacture sutures from copolymers of glycolide and ε-caprolactone.

TABLE 4

Comparison of Inventive Process and Conventional Process BSR Profiles

| BSR | Sample # | | | | | |
|---|---|---|---|---|---|---|
| | 1 Control | 2 43-2 | 3 44-4 | 4 46-2A | 5 46-2B | 6 46-2C |
| 0 Days lbs. | 34.63 | 36.39 | 39.27 | 39.82 | 37.72 | 37.74 |
| 7 Days lbs. | 18.25 | 20.33 | 22.29 | 23.68 | 20.56 | 20.65 |
| Percent Strength Remaining from initial strength | 53% | 56% | 57% | 59% | 55% | 55% |

We claim:

1. A process for producing a suture from a copolymer of glycolide and ε-caprolactone comprising the steps of (a) extruding a melted copolymer of glycolide and ε-caprolactone resin through an orifice and rapidly quenching the melted copolymer resin to produce a filament; (b) drawing the filament in the range of from about 4× to about 7.5× in a first drawing zone to produce a drawn filament; (c) drawing the singly drawn filament in a second drawing zone in the range of from about 1× to about 4× while in a first heated zone being maintained at a temperature in the range of from about 150° F. to about 450° F., to form a doubly drawn filament; (d) relaxing the doubly drawn filament in the range of from about 0.75× to about 0.98×, in a second heated zone being maintained at a temperature in the range of from about 100° F. to about 400° F., to form a relaxed filament; then rack annealing the relaxed filament to form a glycolide/ε-caprolactone suture.

2. The process of claim 1 wherein the filament in the second drawing zone is exposed to a first heated zone being maintained at a temperature in the range of from about 175° F. to about 400° F.

3. The process of claim 2 wherein the filament is drawn by a second and a third godets.

4. The process of claim 2 wherein the doubly drawn filament is maintained second heated zone in the range of from about 3 seconds to about 20 seconds.

5. The process of claim 2 wherein the singly drawn filament is drawn in the range of from about 1× to about 3× the second drawing zone.

6. The process of claim 1 wherein the filament is drawn in a single step in the first draw zone.

7. A process for producing a suture from a copolymer of glycolide and ε-caprolactone comprising the steps of (a) extruding a melted copolymer of glycolide and ε-caprolactone resin through an orifice and rapidly quenching the melted copolymer resin to produce a filament; (b) drawing the filament in the range of from about 4× to about 7.5× in a first drawing zone, to produce a drawn filament; (c) drawing the drawn filament in a second drawing zone in the range of from about 1.0× to about 1.9× while in a first heated zone being maintained at a temperature in the range of from about 150° F. to about 450° F., to form a doubly drawn filament; (d) relaxing the doubly drawn filament in the range of from about 0.75× to about 0.98×, in a second heated zone being maintained at a temperature in the range of from about 150° F. to about 350° F., to form a relaxed filament; then rack annealing the relaxed filament at a temperature of from about 85° C. to about 125° C. for at least 4 to 8 hours to form a glycolide/ε-caprolactone suture.

8. The process of claim 7 wherein the total draw ratio of the suture from drawing and relaxing is in the range of from about 6 to about 8.

9. The process of claim 7 wherein the relaxed filament is annealed for in the range of from about 5 hours to about 7 hours.

10. A suture made from a copolymer of glycolide and ε-caprolactone made by (a) extruding a melted copolymer of glycolide and ε-caprolactone resin through an orifice and rapidly quenching the melted copolymer resin to produce a filament; (b) drawing the filament in the range of from about 4× to about 7.5× in a first drawing zone, to produce a drawn filament; (c) drawing the drawn filament in a second drawing zone in the range of from about 1.0× to about 4× while in a first heated zone being maintained at a temperature in the range of from about 150° F. to about 450° F., to form a doubly drawn filament; (d) relaxing the doubly drawn filament in the range of from about 0.75× to about 0.98×, in a second heated zone being maintained at a temperature in the range of from about 100° F. to about 400° F., to form a relaxed filament; then rack annealing the relaxed filament at a temperature of from about 85° C. to about 125° C. for at least 4 to 8 hours to form a glycolide/ε-caprolactone suture.

* * * * *